(12) United States Patent
Herrmann et al.

(10) Patent No.: US 6,897,659 B2
(45) Date of Patent: May 24, 2005

(54) DEVICE FOR TESTING THE QUALITY OF ROPE-LIKE MATERIALS

(75) Inventors: Rainer Herrmann, Hamburg (DE); Manfred Tews, Hamburg (DE); Udo Schlemm, Hamburg (DE)

(73) Assignee: TEWS Elektronik, Hamburg (DE)

(*) Notice: Subject to any disclaimer, the term of this patent is extended or adjusted under 35 U.S.C. 154(b) by 0 days.

(21) Appl. No.: 10/459,877

(22) Filed: Jun. 12, 2003

(65) Prior Publication Data

US 2004/0017207 A1 Jan. 29, 2004

(30) Foreign Application Priority Data

Jun. 12, 2002 (EP) .............................................. 02013000

(51) Int. Cl.⁷ .............................................. G01R 27/04
(52) U.S. Cl. ...................... 324/633; 324/634; 324/643; 324/71.1
(58) Field of Search ................................. 324/633–636, 324/652, 655, 668, 76.51, 71.1, 73.1, 643, 456, 451, 452

(56) References Cited

U.S. PATENT DOCUMENTS

| | | | |
|---|---|---|---|
| 4,676,651 A | 6/1987 | Beckstein | 356/429 |
| 4,899,100 A | 2/1990 | Talanker et al. | 324/636 |
| 4,904,928 A * | 2/1990 | Lewis | 324/636 |
| 5,175,239 A * | 12/1992 | Gauntt et al. | 528/348 |
| 5,397,993 A | 3/1995 | Tews et al. | 324/634 |
| 5,554,935 A | 9/1996 | Kraszewski et al. | 324/637 |
| 5,764,068 A * | 6/1998 | Katz et al. | 324/727 |
| 6,163,158 A | 12/2000 | Moeller et al. | 324/633 |
| 6,452,404 B2 | 9/2002 | Moeller et al. | 324/633 |
| 6,476,619 B1 | 11/2002 | Moshe et al. | 324/634 |
| 6,747,460 B2 * | 6/2004 | Moller et al. | 324/636 |

FOREIGN PATENT DOCUMENTS

| | | |
|---|---|---|
| DE | OS 20 41 044 | 2/1972 |
| DE | 29 12 558 C2 | 1/1983 |
| DE | 32 37 357 C2 | 12/1985 |
| DE | 43 42 288 A1 | 6/1995 |
| DE | 298 23 928 U 1 | 3/2000 |
| EP | 0 266 611 A2 | 10/1987 |
| EP | 1 035 413 A2 | 9/2000 |
| WO | WO 91/12518 | 8/1991 |
| WO | WO 00/12974 | 3/2000 |

OTHER PUBLICATIONS

Table 7.1, p. 290 of Elements of ELectromagnetics; Second Edition.*
European Search Report for EP 02 01 3000, dated Nov. 14, 2002.
Patent Abstracts of Japan for Publication No. 63210757, publication date Jan. 9, 1988.

* cited by examiner

Primary Examiner—Vincent Q. Nguyen
(74) Attorney, Agent, or Firm—Alix, Yale & Ristas, LLP

(57) ABSTRACT

A device for testing the quality of rope-like materials in the form of yarns, rollings, fiber bands and the like employs a microwave resonator and devices for determining the displacement of the resonant frequency and the widening of the resonance curve due to the rope-like material present in the microwave resonator. Mechanical devices are provided for transporting the rope-like materials through the measuring volume of the microwave resonator. The microwave field is homogeneous in the measuring volume and the measuring device is a microwave generator constructed for measuring the mass per length and the moisture of the rope-like materials. Sensitivity of the device is improved by using metallic elements to concentrate the electromagnetic field in the measuring volume.

15 Claims, 8 Drawing Sheets

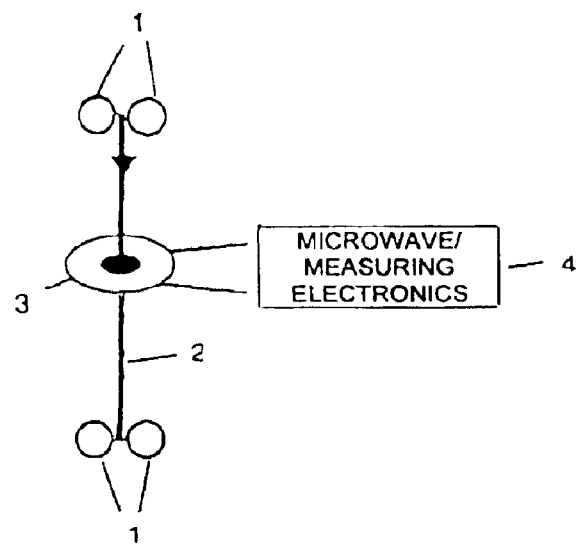
Fig. 1
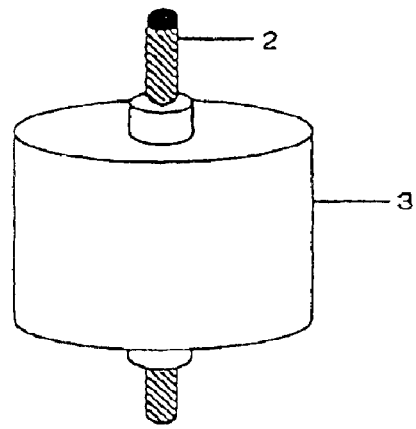
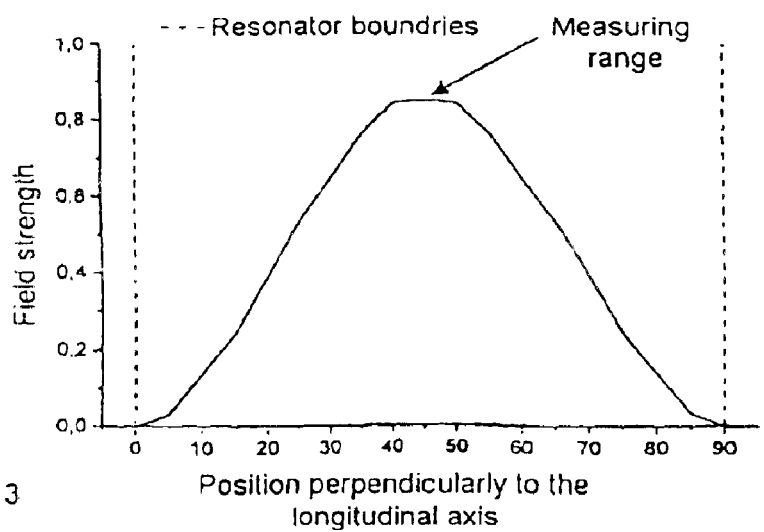
Fig. 2
Fig. 3

DEVICE FOR TESTING THE QUALITY OF ROPE-LIKE MATERIALS

This application claims priority from European Patent Application No. 02013000.1, filed Jun. 12, 2002.

BACKGROUND OF THE INVENTION

1. Field of the Invention

The invention relates to a device for testing the quality of rope-like materials in the form of yarns, rollings, fiber bands and the like by means of a measuring device which has a microwave generator, a microwave resonator and devices for determining the displacement of the resonant frequency and the widening of the resonance curve due to the rope-like material, and with mechanical devices for transporting the rope-like materials through the measuring volume of the microwave resonator.

2. Description of the Related Art

To test the quality of yarns, rollings and fiber bands, it is necessary to detect quality fluctuations, in particular mass fluctuations, i.e. to check their homogeneity. It is then necessary to detect errors with respect to a mass change. The frequency and intensity of the errors can be used for assessing the quality of the material under test. This quality assessment should be preferably but not exclusively done by means of a laboratory test station. The measurement should be independent of parameters such as moisture, color, grading of the material (e.g. area of cultivation of cotton).

Various devices for testing the quality of rope-like materials are known which, however, have disadvantages. The thickness of, in particular, fiber bands, can be mechanically measured by passing the fiber band through a pair of rollers, at least one of which is movable (DE 298 23 928 U1). The deflection of one of the rollers caused by a change in thickness can then be determined by a sensing element. This method may be useful for fiber bands with a constant width. It is not suitable for relatively thin yarns since changes in thickness in the axial direction can only be detected if the rollers are constructed as key and slot rollers as in the prior art.

It is also known to perform measurements of the mass with an arrangement consisting of light transmitter and light receiver (DE 29 12 558 C2). However, this can only be used for measuring optical characteristics due to surface reflections which then do not reproduce the mass or mass per length of material. Falsifications can occur, e.g. in the case of fluctuations of the color of the rope to be measured. This method according to the prior art is also primarily intended for fiber bands.

This defect is also present in a method in which sound is transmitted through the material and changes in the properties of the material are inferred from the change in attenuation (DE 32 37 357 C2). An unambiguous determination of the mass is not possible by this means since the attenuation can also be influenced by other properties, e.g. the moisture of the material. In addition, this method cannot really be used for relatively thin yarns since it is not possible to direct the total sound through the yarn.

Furthermore, it is known to allow the rope-like material to pass through two plates of a capacitor (DE-OS 20 41 044). Such capacitive measuring methods have the disadvantage that the signals respond very sensitively to changes in the moisture because of the high dielectric constant of water. As a result, it is not possible to compensate for the influence of moisture variations. Before the capacitive measurement, therefore, the material must be stabilized to a precisely defined and known moisture value which can easily require one to two days even with uniform temperatures and other constant conditions. It is therefore not possible to determine quality quickly. The moisture fluctuations are all the more disturbing the closer to production the textile material is examined in the test station, that is to say if it is not possible to ensure that the material is sufficiently homogenized. An accurate image of the quality of the current product which is free of moisture fluctuations is only obtained after it has been stored for a sufficiently long period of time under corresponding conditions. Even then, however, moisture inhomogeneities set a clear limit to the precision of measurements due to variable pore structures which occur in all products.

In a rope material testing method of the type employing a microwave field (WO 00/12974), the density of the fibrous rope material is determined, i.e. the mass per unit volume is measured. If the volume of the material which is being measured in each case changes, this density determination is only possible if the volume of the sample in the measuring field is known in each case. In addition, the location of the measured volume of the material must be kept exactly constant by mechanical sample guidance, since falsified signals are obtained if the rope material migrates into areas of lesser microwave intensities. If the cross-sectional volume of the sample changes, this must either be detected by a parallel volume measurement or taken into consideration by recalibration for the density measurement. In many cases, the density is also of subordinate significance if the material will later be compressed in any case, that is to say brought to a greater density. The density is, therefore, less suitable for testing quality.

SUMMARY OF THE INVENTION

Aspects of the present invention relate to providing a homogenous microwave field in a measuring volume (space) through which the rope-like material is passed and detecting changes in the resonance curve of the microwave field caused by the rope-like material. The homogeneous microwave field in the measuring volume allows the device to measure the mass per length and the moisture of the rope-like materials.

Thus, in contrast to the prior art, it is not the density of the rope-like materials which are measured but the mass per length. This value is essential for the further processing so that comparable or known quantities of material are always supplied per unit time in downstream machines. The quantity of material supplied per unit time is obtained from the measured mass per length and the feeding rate.

So that the mass per length can be determined accurately, it is provided that the microwave measuring field is essentially homogeneous over the sample volume. It is, therefore, unimportant if the material has changes in its cross-sectional dimensions or moves slightly out of the center of the measuring field. In contrast to the method according to the prior art, the microwave signal will not be affected even if the material is compressed by a factor of 10 (assuming there is no change in the mass per length).

Due to the special design of the microwave resonator field with resonators specially adapted to the product geometry for this purpose, in a device according to the invention, the volume taken up by the rope-like materials when passing through the measuring volume is completely irrelevant to the measured signal as long as they are moved within certain limits which are valid for the special resonator and the specific product. If, therefore, the fiber-like or rope-like material is compressed within these measuring volume limits when passing through the resonator, the mass signal generated by the evaluating circuit remains constant even if the rope density changes by a multiple. This is also one of the reasons why switching to a number of resonators is provided in an advantageous embodiment. Depending on the required volume taken up by the material to be measured, a special resonator is used for measuring the mass which exhibits a homogeneous electrical magnetic field in cross section over the material sample so that a change in mass at any point in the cross section leads to an equivalent change in the mass signal.

In the case of very thin threads, it is useful to limit the necessary transverse homogeneity of the measuring field to a very small cross-sectional area to focus the field on the thread cross sectional area. Focusing the strong and homogenous portion of the field on the thread sectional area amplifies a normally very small measuring effect of the thin thread.

Transverse homogeneity of the measuring field also provides for a constancy of the mass signal even if the sample to be measured moves transversely to the rope direction in the area of the permissible measuring field. The precision of the mass measurement is clearly increased by this aspect of the invention. Since the measuring field in the rope direction is defined by the resonator geometry, the determination of the mass per length of the rope-like material covers the entire mass in the cross section of the sample independently of its distribution or position in the measuring field of the resonator. Thus, the device according to the invention does not detect the mass flow (mass per unit time or product of mass and rope speed) but the mass present in the measuring field, independently of the rope speed.

In this connection, "determining the displacement of the resonant frequency and the widening of the resonance curve" does not mean that this determination is actually and directly performed by examining the resonance curve step by step. This determination can also be performed indirectly by measuring at a few points on the resonance curve and then certain assumptions are made about the shape of this resonance curve.

The measurement is performed by means of microwaves. Microwave technology provides an accurate method for determining quality parameters, particularly the mass, independently of the moisture (WO 91/12518). Microwave measuring technology also allows working at very high speeds of the rope-like material since no mechanically moving parts are provided which must respond to thickness changes. Instead, the entire detection and evaluation process is electronic.

The measurements can be made at frequencies of 300 MHz to 30 GHz. In particular, however, frequencies between 1 GHz to 15 GHz have been found to be particularly suitable.

To provide for accurate measurements, the field of the resonator should be influenced as much as possible by the rope-like material passing through. The field of the resonator should thus be largely concentrated onto the area of space through which the rope-like material passes. Whereas relatively large resonators, through which the material has to pass, are needed for wide fiber bands, relatively small resonators will be used for thinner yarns or rollings. Alternative resonators may be connected to the evaluating circuit via change-over switches so that the resonator through which the material to be measured happens to be passing is always connected to the evaluating circuit. On the other hand, or in addition, the microwave resonators may have elements for changing the microwave field configuration so that the microwave intensity can be concentrated on to the material even in a relatively large resonator through which a material having smaller dimensions is passing.

The device is suitably constructed as a laboratory test station so that the rope-like materials can be checked before processing.

In addition to the aforementioned advantages, particularly in comparison with the capacitive method, microwave technology has the advantage that the device can be taken into operation immediately after being switched on. The microwave devices do not need a warm-up phase as in the case of the sensitive capacitive methods.

The device according to the invention can be used not only for measuring moisture independently of mass. Instead, in particular, an accurate mass measurement is possible in which the influence of the moisture is automatically compensated for, that is to say, moisture-independent mass measurements are possible. The latter is of particular significance since, due to the large dielectric constant of the water, a variation in the moisture of the material has a critical effect as a disturbance of a precise mass measurement. This error source can be eliminated by means of the automatic compensation of the microwave mass measurement value with the aid of the microwave moisture measurement value. The mass measured with the aid of the microwave method thus corresponds to the actual mass of the product. If, in addition, a moisture calibration is performed on the basis of one of the conventional reference methods (which is largely grade-independent within a type of material), the microwave method also enables the dry material mass or the mass with a freely definable target moisture to be measured.

The term "mass" as used in this application corresponds to "mass per unit length".

In an advantageous embodiment, the microwave resonator is a cylindrical resonator operated in $E_{m,n,p}$ mode (where m=0, n=1, and p=0 or "$E_{010}$"), through the longitudinal axis of which the materials are conducted. The subscript m refers to the number of times the field pattern is repeated around the circumference of the cylindrical resonator; the subscript n refers to the number of times the field pattern is repeated from the axis of the cylindrical resonator to its circumference; and the subscript p refers to the number of times the field pattern is repeated along the axis (length) of the cylindrical resonator. Such a microwave field is particularly homogeneous in the area of the longitudinal axis so that this makes it possible to accurately determine the mass per unit length. The material must, therefore, have a much smaller diameter than the microwave resonator and be conducted through the latter.

If the microwave resonator has two half cylinders which define an essentially cuboid measuring volume between them, the length of material can be introduced from the side which, compared with the aforementioned embodiment, means considerable advantages in the case of relatively long ropes. In this case, it is also possible to take an unbroken rope from the measuring volume and insert another unbroken rope.

In another embodiment, the microwave resonator has two cylindrical coaxial λ/4 resonators oscillating in opposite phases, the microwave fields of which are amplified by elongated metallic elements arranged on the longitudinal axis, between which the materials are passed perpendicularly to the longitudinal axis. In this case, too, a very homogeneous measuring field is obtained in the measuring volume between the metallic elements.

In a particularly advantageous embodiment, it is provided that the microwave resonator is a cylindrical coaxial λ/4 resonator with an elongated metallic element which is arranged on the longitudinal axis and which may have at its front end with maximum electrical microwave field strength a semicircular opening and next to it a slot-shaped passage for the materials, which is open toward the outside and which adjoins the metallic element.

The form of the opening given above as semicircular is not critical. It is only necessary for concentrating the electromagnetic field that the elongated metallic element on one hand in the region of the slot is very close to the to the other electrode, which is in this case formed by the closed end portion of the cylindrical resonator. The remainder of the front side may be open. What is essential is that, with the exception of the region of the slot, the elongated metallic element is spaced apart from metallic parts of the front side of the resonator.

In this embodiment, too, the microwave resonator has a slot which is accessible from the outside and in which the microwave field is very homogeneous and into which an endless thread can also be introduced without difficulty.

Thus, the invention creates a device by means of which the quality, particularly the mass per length of rope-like materials in the form of yarns, rollings, fiber bands and the like can be accurately determined. In particular, the device is constructed as a laboratory station. The device may be constructed for connection to a PC for evaluating the data.

BRIEF DESCRIPTION OF THE DRAWINGS

In the text which follows, the invention will be described by means of advantageous embodiments and referring to the accompanying drawings, in which:

FIG. 1 illustrates a basic configuration and use environment for a device exemplary of aspects of the invention;

FIG. 2 is an exterior perspective view of a microwave resonator suitable for use in conjunction with the device;

FIG. 3 is a graphic representation of the microwave field strength as a function of position perpendicular to the longitudinal axis in the resonator of FIG. 2;

DETAILED DESCRIPTION OF SEVERAL EXEMPLARY EMBODIMENTS

The terms "rope" and "rope-like" are equivalent terms as used in this application and are expressly broadly defined to encompass yarns, strings, fiber bundles, braided and twisted ropes, rollings, fiber bands, cords and the like. The rope or rope-like materials may comprise natural or man-made fibers and/or filaments. The terms rope or rope-like are intended to encompass these materials regardless of their shape which may be generally cylindrical, non-cylindrical or flat, as in a fiber band or strap. It will be understood that the terms rope and rope-like as used herein are interchangeable.

FIG. 1 shows the basic configuration of the device according to the invention. The rope-like material 2 is guided via rope guides, shown at 1, through a microwave resonator 3 which is connected to measuring electronics 4. The measuring electronics radiate microwaves into the cavity 3. The microwave radiation coupled out of the cavity is detected. During this process, both the displacement of the resonant frequency and the widening of the resonance curve due to the rope-like material 2 passed through are determined.

Figure 4A:
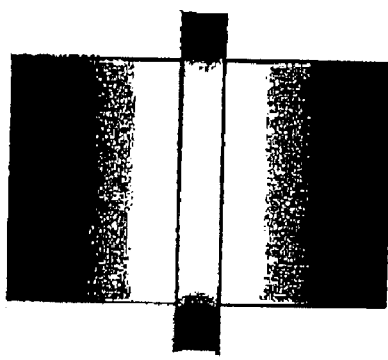
FIGS. 4A and B are longitudinal and cross sectional views of the microwave field strength of the resonator of FIG. 2 with lighter areas indicating a greater microwave field strength.
Figure 4B:
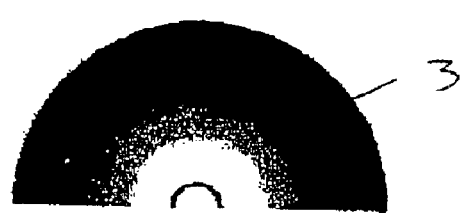

FIG. 2 shows a resonator 3 which is suitable for rope-like material 2 of differing thickness at different operating frequencies. It is suitable for measuring thick fiber bands at low frequencies of up to approx. 5 GHz and for measuring thin yarns at high frequencies. FIG. 3 shows the intensity of the microwave field as a function of the location in the resonator of FIG. 2 perpendicularly to the longitudinal axis. The boundaries of the resonator are indicated by dashed lines. In FIGS. 4A and 4B, the microwave field is shown in a longitudinal section and a cross section, respectively, of the resonator of FIG. 2, with lighter areas indicating greater microwave field strength. These illustrations show that the microwave field strength is essentially homogeneous in the measuring area.

Figure 5:
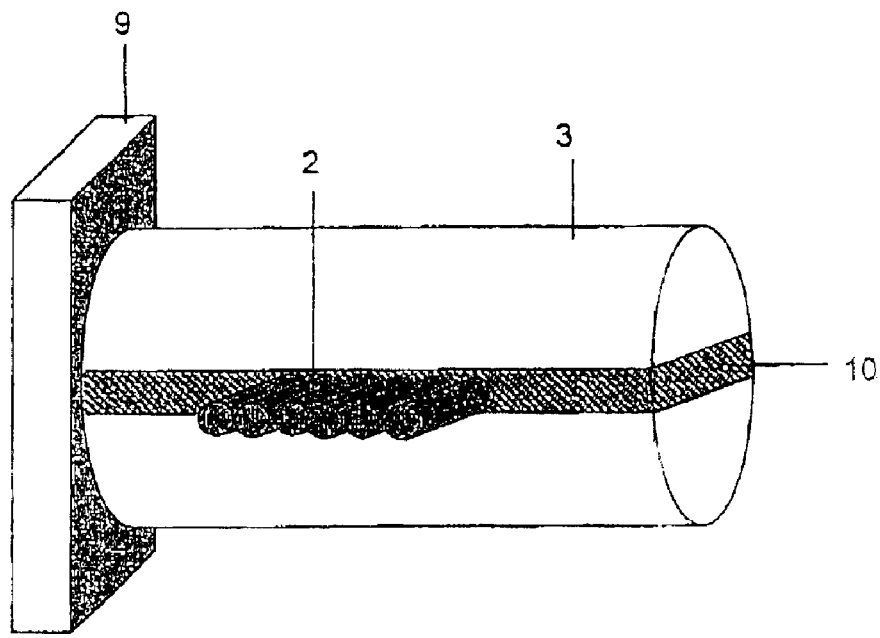
FIG. 5 is an exterior perspective view of an alternative exemplary embodiment illustrative of aspects of the present invention.
Figure 6:
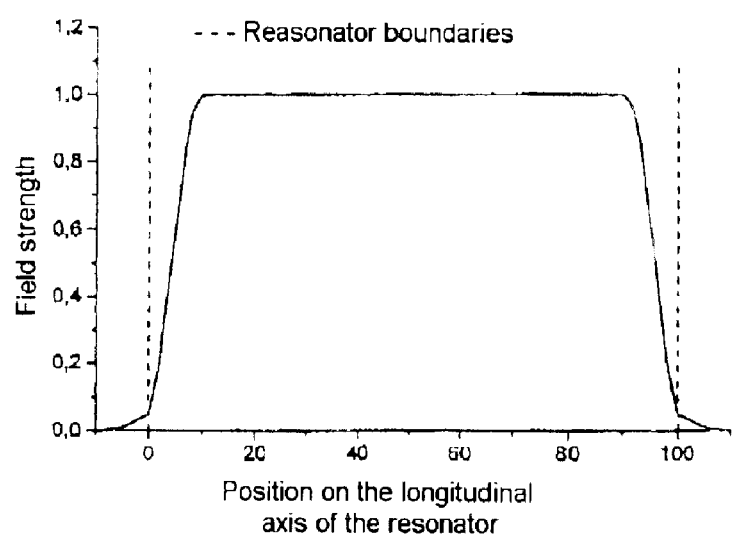
FIG. 6 is a graph illustrating the microwave field strength as a function of location in the resonator of FIG. 5.

FIG. 5 shows a resonator 3 which is suitable for rope-like material which does not have a circular but an elongated cross section. In FIG. 5, a number of circular material ropes 2 arranged next to one another are drawn which are arranged in the measuring volume 10. Naturally, a homogeneous flat material strip could also be measured. The resonator consists of two half cylinders 3 which are arranged at a distance from one another and enclose the measuring volume 10 between themselves. The resonator halves 3 are held by a holder 9. The homogeneous field variation in the measuring volume 10 is graphically plotted in FIG. 6. In addition to the fact that the measuring field is very homogeneous, the resonator of FIG. 5 also offers the advantage that material ropes can be introduced from the side so that endless ropes can also be easily measured.

Figure 7:
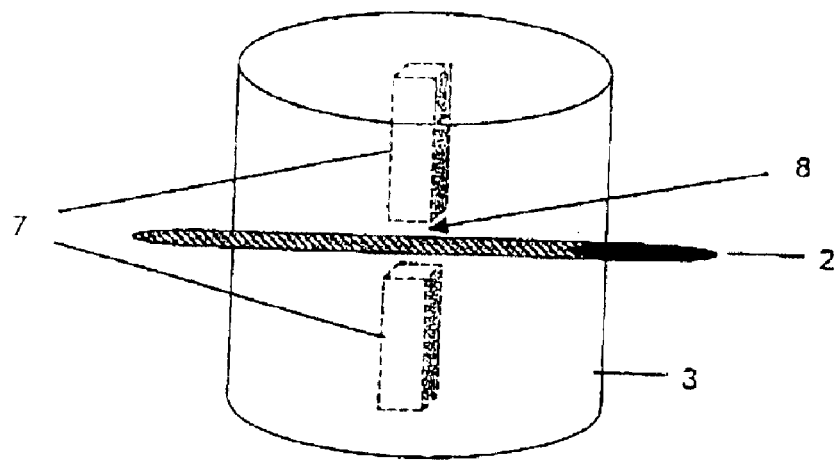
FIG. 7 illustrates a further resonator exemplary of aspects of the present invention.
Figure 8:
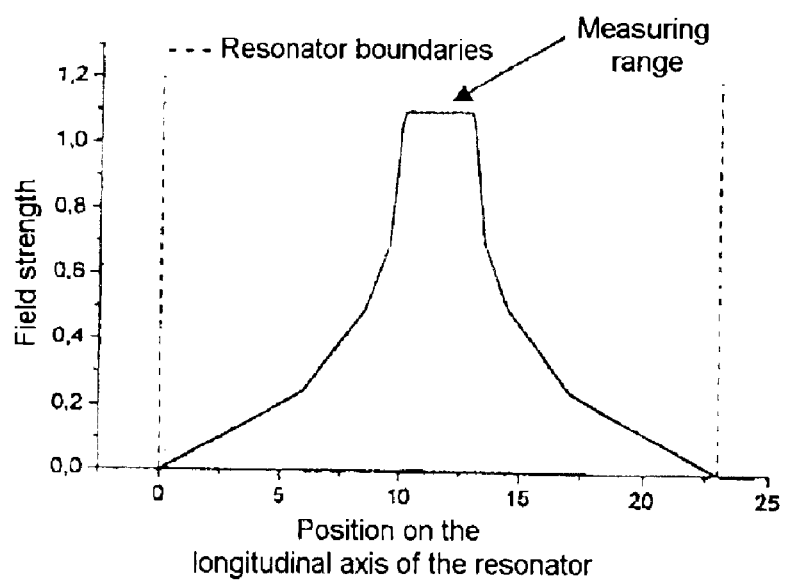
FIG. 8 is a graph illustrating the microwave field strength as a function of location in the resonator of FIG. 7.

In the embodiment of FIG. 7, the resonator consists of two coaxial λ/4 resonators oscillating in opposite phases. This resonator is sensitive enough for measuring even the mass of thin yarns. This is due to the concentration of the field in an area of space 8 through which the material under test 2 is conducted. This concentration is achieved with the aid of metallic elongated elements 7. The variation of the field of this resonator is shown in FIG. 8.

Figure 9:
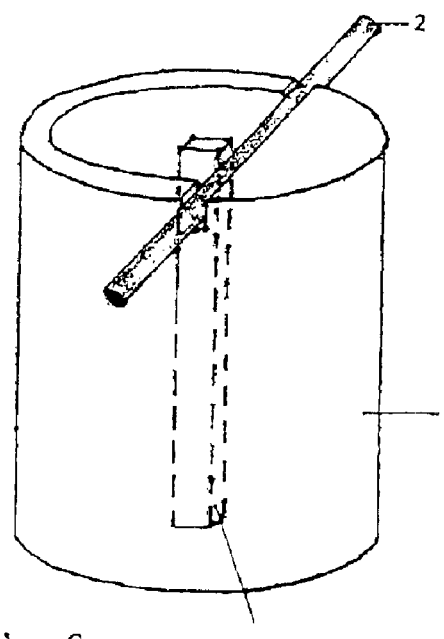
FIG. 9 is a perspective view of a further embodiment of a resonator exemplary of aspects of the present invention.
Figure 10:
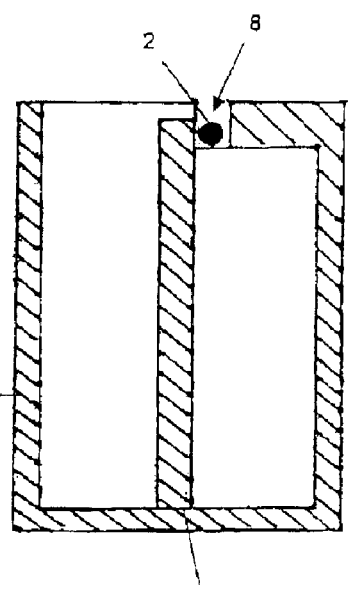
FIG. 10 is a longitudinal sectional view of the resonator of FIG. 9.
Figure 11:
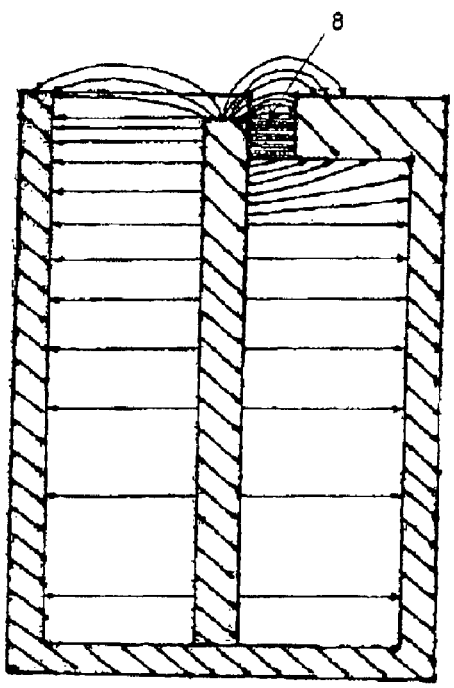
FIG. 11 illustrates the variation of the electrical field strength of the microwave field in the resonator of FIGS. 9 and 10.
Figure 12:
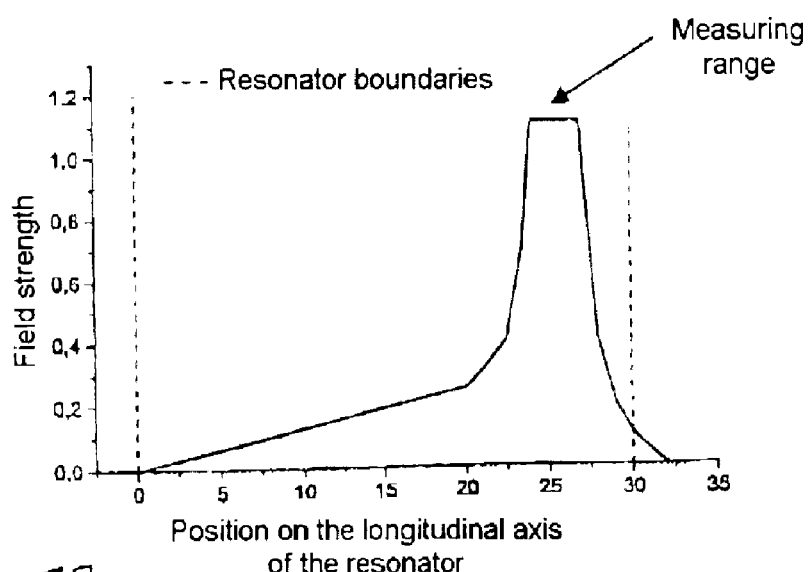
FIGS. 12 and 13 are graphic representations of the microwave field strength as a function of location in the resonator of FIGS. 9 through 11.
Figure 13:
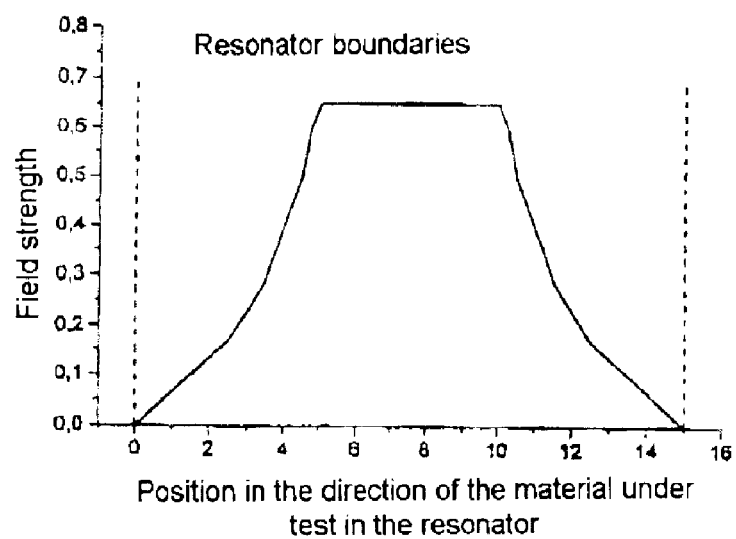

In FIGS. 9 through 11, another resonator is shown which, like the embodiment of FIG. 5, has the advantage that the material rope 2 can be an endless rope which is introduced into a measuring slot. The resonator is a coaxial λ/4 resonator. This means that the field strength is zero at the bottom of the resonator and increases continuously towards the upper edge of the resonator. The height of the resonator corresponds to one quarter of the wavelength. This resonator, too, can be used for measuring the mass of thin yarns due to the concentration of the field in the area of space 8 through which the material under test is conducted. The field concentration is produced with the aid of a rod-shaped metallic element 7 which is located on the longitudinal axis of the resonator, in interaction with the metallic end face. The resonator is cylindrical, the end face at which the microwave field strength is at a maximum, being half metallically open and half metallically closed. The slot for receiving the rope-like material 2 is located slightly eccentrically next to the rod-shaped element 7. The variation of the electrical lines of the field is shown in FIG. 11, a higher density of the lines of the field meaning a higher electrical field strength. In FIGS. 12 and 13, the intensity of the microwave field in the direction of the longitudinal axis of the resonator and in the direction of the material under test 2 is plotted.

Figure 14:
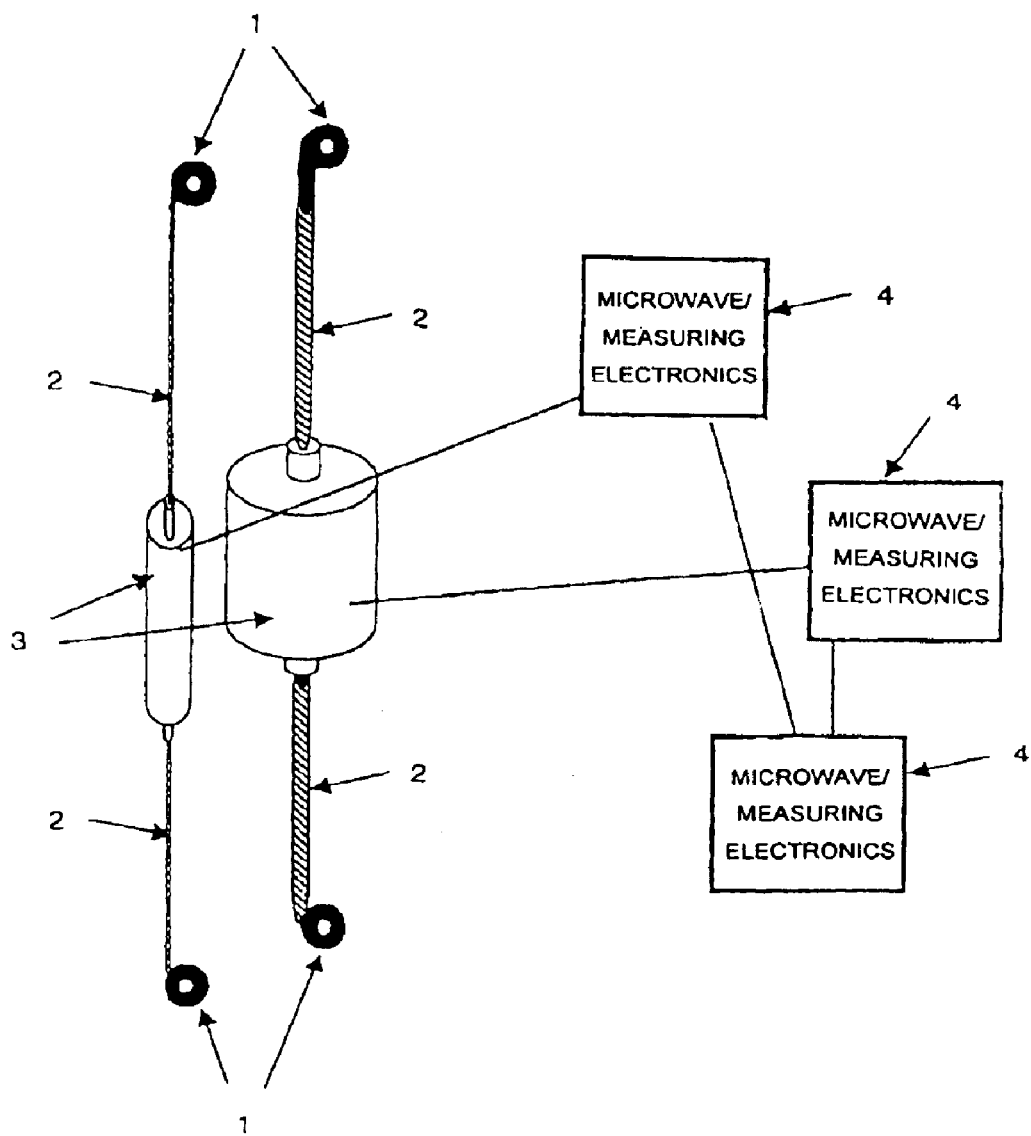
FIG. 14 illustrates an arrangement for measuring various sizes of rope-like materials.

In the embodiment of FIG. 14, a number of resonators 3 which are provided for thin material (on the left) and thick material (on the right) are simultaneously provided. Each of these microwave resonators is connected to its own microwave electronics, the smaller resonator being operated at higher microwave frequencies than the larger one. In this case, the constructional form of the resonators can be the same for all resonators. However, the sizes of the resonators depend on the operating frequency. In the higher frequency range, smaller resonators are operated which are capable of measuring material under test having a very small mass. For thicker fiber bands, in contrast, larger resonators are used at lower frequency. In this case, cylindrical resonators through which material under test passes in the area of the axis of the cylinder are used as possible resonators. For example, the circular cylindrical resonators are operated in $E_{010}$ mode. The diameter of the resonators is dependent on the wavelength.

Figure 15:
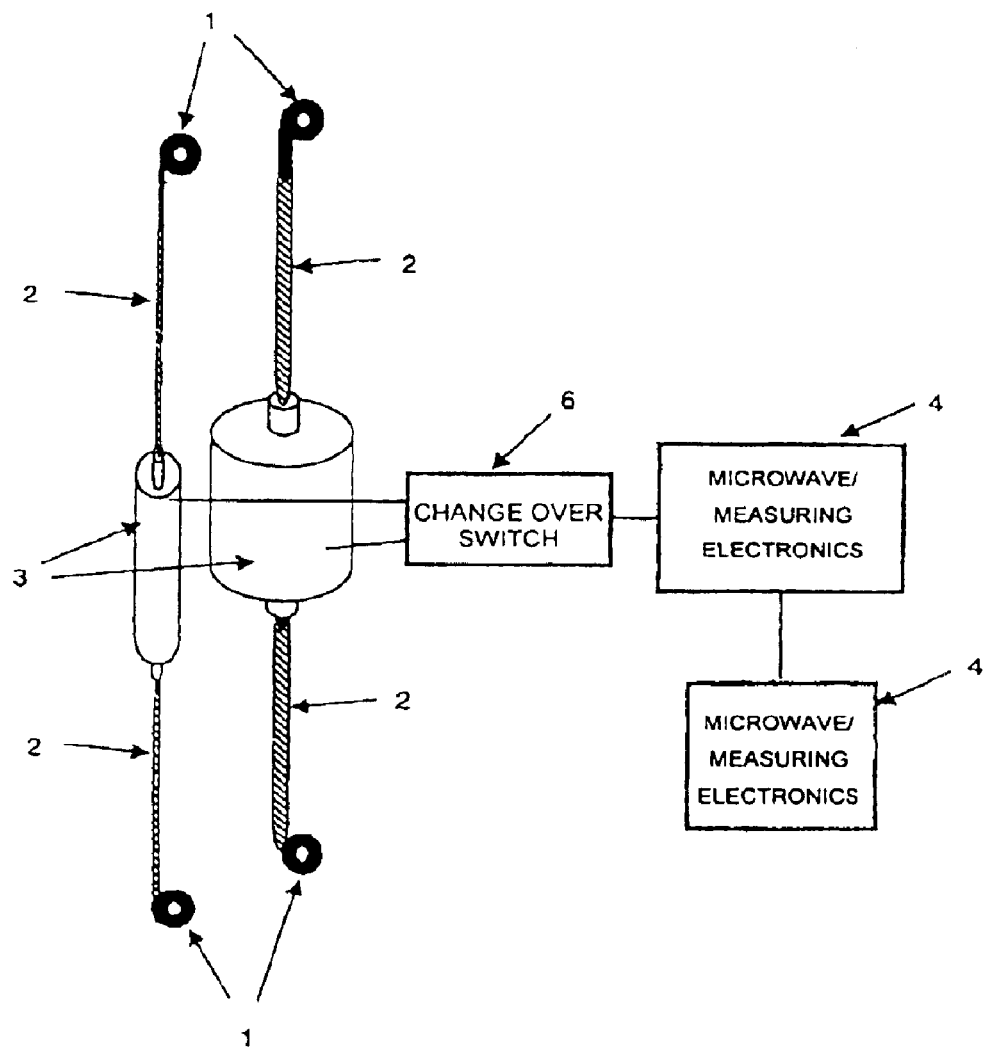
FIG. 15 illustrates another arrangement for measuring various sizes of rope-like materials.

In the embodiment of FIG. 15, only one microwave electronics unit 4 is advantageously provided which is in each case connected by means of a change-over switch 6 to the microwave resonator 3 through which rope-like material 2 is currently being passed. In this case, only one microwave electronics unit in combination with a change-over switch is necessary which drives the various resonators. In the case of measurements in the low range from 2 to 3 GHz, more cylindrical resonators can be used for measuring bands with higher mass. For very thin yarns, the field in the resonator must be concentrated on the smallest space in spite of the relatively long wavelength, to ensure sufficient sensitivity of the resonators.

To provide for an accurate measurement, the microwave field of the resonator 3 should be essentially concentrated on the rope-like material 2, not only in the case of thin yarns. In the embodiment of FIG. 14, this is done by means of resonators of various sizes and having very different resonant frequencies. In the embodiment of FIG. 15, all band masses are measured in the same frequency range. This is done by concentrating the field with the aid of internal structures of the resonators. It is also possible to arrange a number of identical resonators, which are operated at the same frequencies, next to one another in order to measure a number of ropes at the same time.

While exemplary embodiments of the foregoing invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. A measuring device for testing the quality of rope having a mass per length and moisture content, said device comprising:

a microwave resonator comprising two cylindrical coaxial λ/4 resonators oscillating in opposite phases and arranged to produce a substantially homogenous electromagnetic field in a measuring volume configured to receive the rope for testing, said electromagnetic field having a resonant frequency and a resonance curve;

spaced apart elongated metallic elements arranged on the common axis of said resonators to define said measuring volume between said metallic elements;

devices for detecting changes in the resonant frequency and the resonance curve caused by rope present in said measuring volume; and mechanical devices for transporting the rope through said measuring volume perpendicularly to the common axis of said resonators, wherein said measuring device employs said detected changes in the resonant frequency and resonance curve to measure the mass per length and the moisture content of the rope present in said measuring volume.

2. The measuring device of claim 1, wherein said measuring device measures the moisture content of the rope independently of the mass per length.

3. The measuring device of claim 1, wherein said measuring device compensates for said measured moisture content to provide a moisture-independent mass per length measurement.

4. The measuring device of claim 1, wherein the resonator is operated at frequencies between 300 MHz and 30 GHz.

5. The measuring device of claim 1, wherein the resonator is operated at frequencies between 1 GHz and 15 GHz.

6. The measuring device of claim 1, comprising a number of resonators connected to an evaluating circuit via change-over switches.

7. The measuring device of claim 1, wherein said metallic elements concentrate the microwave field in said measuring volume.

8. The measuring device of claim 1, wherein said device is constructed as a laboratory test station.

9. A measuring device for testing the quality of rope having a mass per length and moisture content, said device comprising:

a cylindrical coaxial λ/4 resonator with an elongated metallic element arranged on a longitudinal axis of said resonator, said resonator having a first end with a closed portion, an open portion and defining a slot traversing said first end between one end of said elongated metallic element and said closed portion, the elongated metallic element and closed portion concentrating said electromagnetic field in the measuring volume defined between said one end of the elongated metallic element and said closed portion, said slot being open in a direction away from said resonator, said resonator producing a substantially homogeneous electromagnetic field having a resonant frequency and a resonance curve;

devices for detecting changes in said resonant frequency and said resonant curve caused by rope present in said measuring volume; and mechanical devices for transporting the rope through said measuring volume, wherein said measuring device employs said detected changes in the resonant frequency and resonance curve to measure the mass per length and the moisture content of the rope present in said measuring volume.

10. The measuring device of claim 9, wherein said device permits measurement of a portion of a length of unbroken rope by insertion into said measuring volume through said slot open end.

11. A method for testing the quality of rope comprising:

generating a microwave field in a cylindrical coaxial $\lambda/4$ resonator to produce a substantially homogenous electromagnetic field in a measuring volume;

concentrating said electromagnetic field in said measuring volume by means of metallic elements, at least one of said metallic elements arranged on a longitudinal axis of said resonator;

feeding the rope through said measuring volume perpendicularly to said longitudinal axis;

detecting changes to the resonance frequency and resonance curve of said electromagnetic field caused by the rope present in said measuring volume; and producing measured values from said detected changes, said measured values corresponding to the mass per length and moisture content of the rope present in the measuring volume.

12. The method of claim 11, wherein said step of producing comprises:

using the measured value corresponding to the moisture content of the rope to produce a moisture-independent measured value corresponding to the mass per length of the rope.

13. The method of claim 11, comprising:

providing a slot in communication with said measuring volume, wherein said step of feeding comprises passing said rope through said slot and said measuring volume.

14. The method of claim 11, wherein said step of generating comprises:

operating a microwave resonator at a frequency in the range of 300 MHz to 30 GHz.

15. The method of claim 11, wherein said step of generating comprises:

operating a microwave resonator at a frequency in the range of 1 GHz to 15 GHz.

* * * * *